(12) United States Patent
Murray, III et al.

(10) Patent No.: US 9,173,738 B2
(45) Date of Patent: *Nov. 3, 2015

(54) TRANSCATHETER PROSTHETIC HEART VALVE DELIVERY SYSTEM AND METHOD WITH CONTROLLED EXPANSION OF PROSTHETIC HEART VALVE

(71) Applicant: Medtronic, Inc., Minneapolis, MN (US)

(72) Inventors: Robert J. Murray, III, Santa Rosa, CA (US); Charles Tabor, St. Louis Park, MN (US); Andrew Crisman, Shoreview, MN (US); Adam Shipley, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/095,465

(22) Filed: Dec. 3, 2013

(65) Prior Publication Data

US 2014/0172075 A1 Jun. 19, 2014

Related U.S. Application Data

(62) Division of application No. 13/091,917, filed on Apr. 21, 2011, now Pat. No. 8,623,075.

(60) Provisional application No. 61/326,310, filed on Apr. 21, 2010.

(51) Int. Cl.
*A61F 2/24* (2006.01)

(52) U.S. Cl.
CPC .............. *A61F 2/2418* (2013.01); *A61F 2/2436* (2013.01); *A61F 2/2439* (2013.01); *A61F 2230/0054* (2013.01)

(58) Field of Classification Search
USPC .............. 623/1.11, 2.11, 2.17, 2.37; 606/191, 606/194, 198; 604/104, 509
See application file for complete search history.

(56) References Cited

U.S. PATENT DOCUMENTS

| 5,683,451 | A | 11/1997 | Lenker et al. |
| 5,824,041 | A | 10/1998 | Lenker et al. |
| 5,906,619 | A | 5/1999 | Olson et al. |
| 5,957,949 | A | 9/1999 | Leonhardt et al. |
| 7,101,396 | B2 | 9/2006 | Artof et al. |
| 7,105,016 | B2 | 9/2006 | Shiu et al. |
| 8,313,525 | B2 | 11/2012 | Tuval et al. |

(Continued)

FOREIGN PATENT DOCUMENTS

| GB | 2433700 | 7/2007 |
| WO | 2006/076890 | 7/2006 |

(Continued)

*Primary Examiner* — Vy Bui

(57) ABSTRACT

A delivery system for use with a prosthetic heart valve having a stent frame to which a valve structure is attached includes a shaft assembly including a distal end, an intermediate portion, and a first coupling structure disposed near the distal end and configured to be coupled to a distal end of the prosthetic heart valve via a first tether. A sheath assembly defines a lumen sized to slidably receive the shaft assembly. The delivery system is configured to transition from a loaded state in which the sheath assembly encompasses the prosthetic heart valve to a deployed state in which the sheath assembly is withdrawn from the prosthetic heart valve. The first coupling structure is configured to be manipulated in a first direction to provide a controlled expansion or contraction of the distal end of the prosthetic heart valve.

11 Claims, 6 Drawing Sheets

(56) References Cited

U.S. PATENT DOCUMENTS

| | | | |
|---|---|---|---|
| 8,323,335 B2 * | 12/2012 | Rowe et al. | 623/2.11 |
| 8,337,541 B2 * | 12/2012 | Quadri et al. | 623/1.11 |
| 8,403,981 B2 * | 3/2013 | Forster et al. | 623/2.11 |
| 2003/0199963 A1 | 10/2003 | Tower et al. | |
| 2005/0137688 A1 | 6/2005 | Salahieh et al. | |
| 2006/0004439 A1 | 1/2006 | Spenser et al. | |
| 2006/0052867 A1 | 3/2006 | Revuelta et al. | |
| 2006/0229561 A1 | 10/2006 | Huszar | |
| 2006/0259136 A1 | 11/2006 | Nguyen et al. | |
| 2006/0265056 A1 | 11/2006 | Nguyen et al. | |
| 2007/0005131 A1 | 1/2007 | Taylor | |
| 2007/0088431 A1 | 4/2007 | Bourang et al. | |
| 2007/0203561 A1 | 8/2007 | Forster et al. | |
| 2007/0233223 A1 | 10/2007 | Styrc | |
| 2007/0239266 A1 | 10/2007 | Birdsall | |
| 2007/0239269 A1 | 10/2007 | Dolan et al. | |
| 2008/0021546 A1 | 1/2008 | Patz et al. | |
| 2008/0065011 A1 | 3/2008 | Marchand et al. | |
| 2008/0082165 A1 | 4/2008 | Wilson et al. | |
| 2008/0147160 A1 | 6/2008 | Ghione et al. | |
| 2008/0147181 A1 | 6/2008 | Ghione et al. | |
| 2008/0188928 A1 | 8/2008 | Salahieh et al. | |
| 2008/0262590 A1 | 10/2008 | Murray | |
| 2009/0093876 A1 | 4/2009 | Nitzan et al. | |
| 2009/0138079 A1 | 5/2009 | Tuval et al. | |
| 2009/0171447 A1 | 7/2009 | Von Segesser et al. | |
| 2009/0177275 A1 | 7/2009 | Case | |
| 2009/0281619 A1 | 11/2009 | Le et al. | |
| 2010/0082089 A1 | 4/2010 | Quadri et al. | |
| 2010/0094411 A1 | 4/2010 | Tuval et al. | |
| 2010/0121434 A1 | 5/2010 | Paul et al. | |

FOREIGN PATENT DOCUMENTS

| | | |
|---|---|---|
| WO | 2007/071436 | 6/2007 |
| WO | 2008/138584 | 11/2008 |
| WO | 2009/091509 | 7/2009 |

* cited by examiner

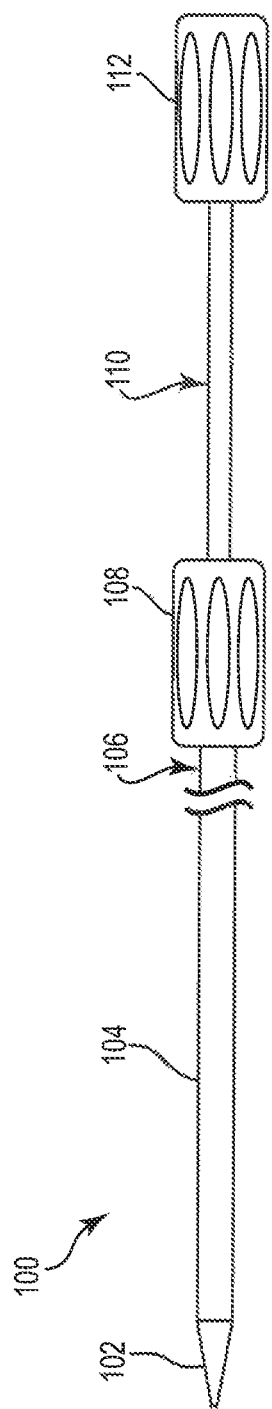

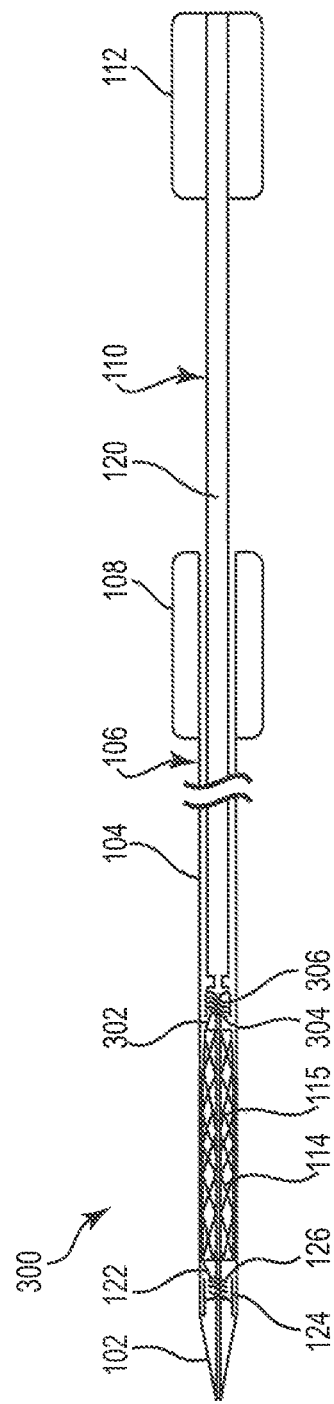

TRANSCATHETER PROSTHETIC HEART VALVE DELIVERY SYSTEM AND METHOD WITH CONTROLLED EXPANSION OF PROSTHETIC HEART VALVE

CROSS-REFERENCE TO RELATED APPLICATIONS

This application is a Division of and claims priority to U.S. patent application Ser. No. 13/091,917 filed Apr. 21, 2011, which claims priority under 35 U.S.C. §119(e)(1) to U.S. Provisional Patent Application Ser. No. 61/326,310, filed Apr. 21, 2010, entitled "Transcatheter Prosthetic Heart Valve Delivery System and Method With Controlled Expansion of Prosthetic Heart Valve"; the entire teachings of which are incorporated herein by reference.

BACKGROUND

The present disclosure relates to systems and methods for percutaneous implantation of a heart valve prosthesis. More particularly, it relates to delivery systems and methods for transcatheter implantation of a stented prosthetic heart valve.

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement has become a routine surgical procedure for patients suffering from valve regurgitation or stenotic calcification of the leaflets. Conventionally, the vast majority of valve replacements entail full stenotomy in placing the patient on cardiopulmonary bypass. Traditional open surgery inflicts significant patient trauma and discomfort, requires extensive recuperation times, and may result in fife-threatening complications.

To address these concerns, within the last decade, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally-invasive surgical methods. In such methods, a valve prosthesis is compacted for delivery in a catheter and then advanced, for example through an opening in the femoral artery and through the descending aorta to the heart, where the prosthesis is then deployed in the valve annulus (e.g., the aortic valve annulus).

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vein segment or pericardial manufactured tissue valve that is mounted in some manner within an expandable stent frame to make a valved stent. In order to prepare such a valve for percutaneous implantation, one type of valved stent can be initially provided in an expanded or uncrimped condition, then crimped or compressed around a balloon portion of a catheter until it is close to the diameter of the catheter. In other percutaneous implantation systems, the stent frame of the valved stent can be made of a self-expanding material. With these systems, the valved stent is crimped down to a desired size and held in that compressed state with a sheath, for example. Retracting the sheath from this valved stent allows the stent to expand to a larger diameter, such as when the valved stent is in a desired position within a patient. With either of these types of percutaneous stent delivery systems, conventional sewing of the prosthetic heart valve to the patient's native tissue is typically not necessary.

It is imperative that the stented heart valve prosthesis be accurately located relative to the native annulus prior to full deployment from the catheter. Successful implantation requires that the transcatheter prosthetic heart valve intimately lodge and seal against the native annulus. A self-expanding transcatheter heart valve must have a high radial force when expanding to properly anchor itself in the anatomy of the heart. If the prosthetic is incorrectly positioned relative to the native annulus, serious complications can result as the deployed device will leak and even may dislodge from the implantation site. Greatly complicating this effort is the fact that once the heart valve prosthesis (e.g., a self-deploying stent) is deployed from the catheter, it is exceedingly difficult to re-collapse or "recapture" the prosthetic with conventional delivery tools (e.g., an outer sheath or catheter). This same concern does not arise in the context of other vascular stents; with these procedures, if the target site was "missed," another stent is simply deployed to "make-up" the difference. In short, recapturing a deployed or partially deployed stent-based device is unique to transcatheter heart valves.

While imaging technology can be employed as part of the implantation procedure to assist a clinician in better evaluating a location of the transcatheter prosthetic heart valve immediately prior to deployment, in many instances, this evaluation alone is insufficient. Instead, clinicians desire the ability to partially deploy the prosthesis and then evaluate a position relative to the native annulus prior to full deployment. While in theory the "re-capturing" of a partially deployed stented prosthetic heart valve is straight forward, in actual practice, the constraints presented by the implantation site and the stented heart valve itself render the technique exceedingly difficult.

In light of the above, although there have been advances in percutaneous valve replacement techniques and devices, there is a continued desired to provide different delivery systems for delivering and repositioning cardiac replacement valves, and in particular self-expanding stented prosthetic heart valves, to an implantation site in a minimally invasive and percutaneous manner. There is also a continuing desire to be able to provide a more controlled deployment of replacement valves, and to be able to reposition and/or retract the valves once they have been deployed or partially deployed in order to ensure optimal placement of the valves within the patient.

SUMMARY

One embodiment is directed to a delivery system for use with a prosthetic heart valve having a stent frame to which a valve structure is attached. The delivery system includes a shaft assembly including a distal end, an intermediate portion, and a first coupling structure disposed near the distal end and configured to be coupled to a distal end of the prosthetic heart valve via a first tether. A sheath assembly defines a lumen sized to slidably receive the shaft assembly. The delivery system is configured to transition from a loaded state in which the sheath assembly encompasses the prosthetic heart valve to a deployed state in which the sheath assembly is withdrawn from the prosthetic heart valve. The first coupling structure is configured to be manipulated in a first direction to provide a controlled expansion or contraction of the distal end of the prosthetic heart valve.

Another embodiment is directed to a system for performing a therapeutic procedure on a defective heart valve of a patient. The system includes a delivery system including a shaft assembly and a sheath assembly. The shaft assembly includes a distal end and a first coupling structure disposed near the distal end and configured to be coupled to a distal end of the prosthetic heart valve via a first tether. The sheath assembly defines a lumen sized to slidably receive the shaft assembly. The system includes a prosthetic heart valve having a stent frame and a valve structure attached to the frame. The valve structure forms at least two valve leaflets. The prosthetic heart valve is self-expandable from a compressed arrangement to a natural arrangement. The delivery system is configured to slidably receive the prosthetic heart valve within the sheath assembly and is configured to be operable to transition from a loaded state in which the sheath assembly encompasses the prosthetic heart valve to a deployed state in which the sheath assembly is withdrawn from the prosthetic heart valve to permit the prosthetic heart valve to self-expand to the natural arrangement and release from the delivery system. The first coupling structure is configured to be rotated in a first direction to provide a controlled expansion of the distal end of the prosthetic heart valve and is configured to be rotated in a second direction to provide a controlled contraction of the distal end of the prosthetic heart valve.

Yet another embodiment is directed to a method of performing a therapeutic procedure on a defective heart valve of a patient. The method includes receiving a delivery system loaded with a self-expanding prosthetic heart valve having a stent frame to which a valve structure is attached. The delivery system includes a shaft assembly slidably positioned within a delivery sheath. The shaft assembly includes a first coupling structure disposed near a distal end of the shaft assembly and coupled to a distal end of the prosthetic heart valve via a first tether. The delivery sheath contains the prosthetic heart valve in a compressed arrangement. The method includes manipulating the delivery system to guide the prosthetic heart valve through the patient's vasculature and into the defective heart valve, and withdrawing the delivery sheath from the prosthetic heart valve. The first coupling structure is rotated in a first direction to provide a controlled expansion of the distal end of the prosthetic heart valve, and the prosthetic heart valve is released from the delivery system.

BRIEF DESCRIPTION OF THE DRAWINGS

FIGS. 1A-1C are diagrams illustrating a system for delivering a transcatheter prosthetic heart valve to an implantation site according to one embodiment.

FIG. 3 is a diagram illustrating a system for delivering a transcatheter prosthetic heart valve to an implantation site according to another embodiment.

DETAILED DESCRIPTION

The terms "distal" and "proximal" are used herein with reference to the treating clinician during the use of the catheter system; "Distal" indicates an apparatus portion distant from, or a direction away from the clinician and "proximal" indicates an apparatus portion near to, or a direction towards the clinician. The term "therapy" or "therapeutic procedure" as used herein in the context of heart valves is intended to include the repair of a heart valve, the replacement of a heart valve, or a combination of repair and replacement of a heart valve. While some of the description herein may refer specifically to therapy of aortic valves, the systems and methods disclosed herein can also generally be used for therapy of native or bioprosthetic mitral, pulmonic, or tricuspid valves.

Figure 1B:
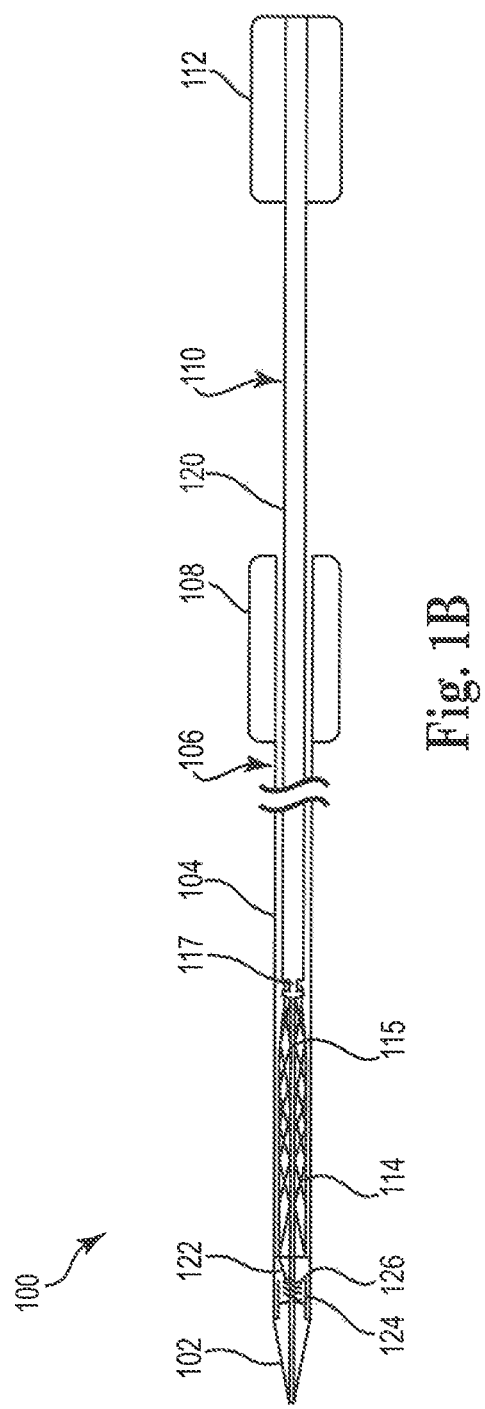
Figure 1C:
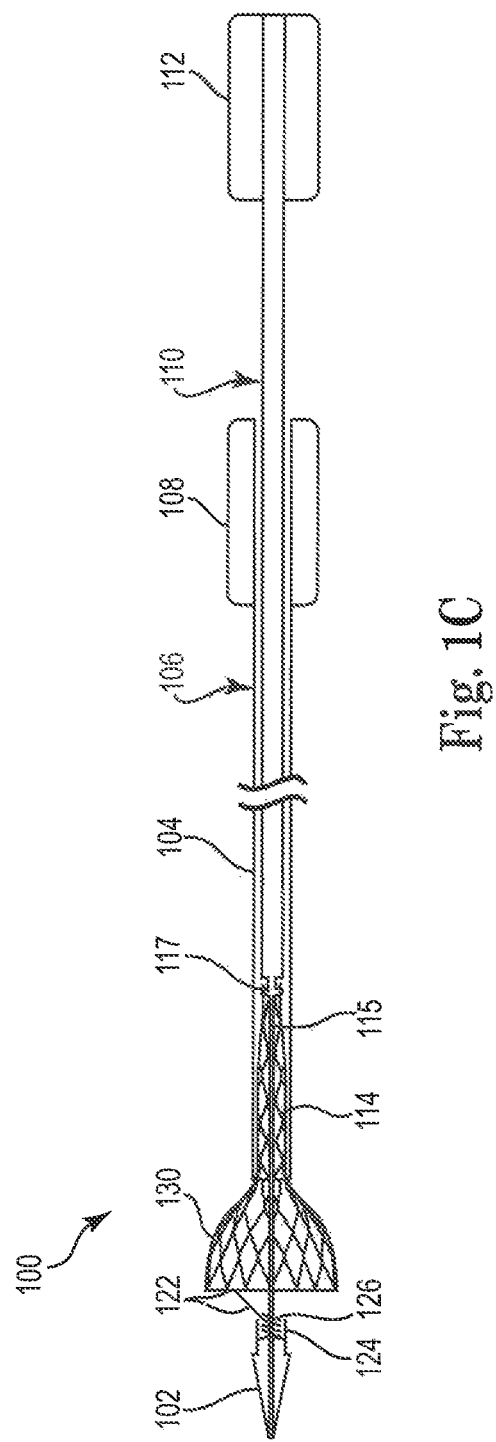

FIGS. 1A-1C are diagrams illustrating a system 100 for delivering a transcatheter prosthetic heart valve to an implantation site according to one embodiment. In the illustrated embodiment, the system 100 includes a shaft assembly 110 and a sheath assembly 106. The shaft assembly 110 includes a handle device 112, a carrier shaft 120, a connector shaft 115, a nose cone 102, a coupling structure 126, and a sleeve 124. The connector shaft 115 interconnects the carrier shaft 120 and the nose cone 102, and in some constructions has a reduced-sized diameter to permit placement of a prosthetic heart valve 114 over the connector shaft 115. The nose cone 102 is disposed at the distal end of the shaft assembly 110. Though not shown in FIGS. 1A-1C, a guide wire lumen can be formed through the shafts 115 and 120.

Carrier shaft 120 is sized to be slidably received within the sheath assembly 106, and is configured in the illustrated embodiment for releasable coupling with the prosthetic heart valve 114. The carrier shaft 120 forms or includes a coupling device 117. The coupling device 117 is configured to selectively retain a proximal portion of the prosthetic heart valve 114. The coupling device 117 is configured to releasably mount the prosthetic heart valve 114 to the shaft assembly 110 when the prosthetic heart valve 114 is forced to a collapsed state within the sheath assembly 106. In this collapsed state, then, the prosthetic heart valve 114 will longitudinally move with movement of the shaft assembly 110. The sheath assembly 106 is configured to permit deployment of the prosthetic heart valve 114 from the loaded state shown in FIGS. 1A and 1B. The delivery system 100 is configured to transition from the loaded state in which the sheath assembly 106 encompasses the prosthetic heart valve 114 to a deployed state in which the sheath assembly 106 is withdrawn from the prosthetic heart valve 114.

The sleeve 124 and the coupling structure 126 are disposed near the distal end of the shaft assembly 110. The sleeve 124 and the coupling structure 126 are attached to a proximal end of the nose cone 102, and extend proximally from the proximal end of the nose cone 102 toward the prosthetic heart valve 114. In the illustrated embodiment, the coupling structure 126 is a coil spring. In one embodiment, the sleeve 124 is a transparent tube and covers at least a portion of the coupling structure 126. The distal end of the prosthetic heart valve 114 is releasably coupled to the coupling structure 126 via a tether 122, such as a suture. In one embodiment, the tether 122 includes a first portion that forms a loop, which is attached to the distal end of the prosthetic heart valve 114, and a second portion, which is attached to the coupling structure 126. The coupling structure 126 is configured to be rotated to provide a controlled expansion and contraction of the distal end of the prosthetic heart valve 114. In one embodiment, a clinician rotates the handle device 112 in a desired direction (e.g., clockwise or counterclockwise), which causes a corresponding rotation of the shaft assembly 110, including the coupling structure 126. The coupling structure 126 is also configured to be longitudinally translated to provide a controlled expansion and contraction of the distal end of the prosthetic heart valve 114. In one embodiment, a clinician longitudinally translates the handle device 112 in a desired direction (e.g., in a proximal direction or in a distal direction), which causes a corresponding longitudinal translation of the shaft assembly 110, including the coupling structure 126. The sleeve 124 helps to guide the tether 122 during the expansion and contraction of the prosthetic heart valve 114.

The nose cone 102 can assume a variety of forms, and is generally constructed to facilitate atraumatic placement of the delivery system 100 through a patient's vasculature and heart. The handle device 112 is mounted or connected to a proximal end of the carrier shaft 120, and provides a convenient surface for grasping by a clinician.

The sheath assembly 106 generally includes a sheath 104 and a handle device 108. The sheath 104 can be of a conventional catheter-like configuration (e.g., biocompatible polymer with or without an encapsulated wire braiding). In some constructions, the sheath 104 can further incorporate various steering features. Regardless, the sheath 104 is generally compliant, and is able to traverse the tortuous pathways associated with transcatheter heart valve implantation. The handle device 108 can assume a wide variety of forms, and is generally mounted or connected to a proximal end of the sheath 104. The sheath 104 defines a lumen sized to slidably receive the carrier shaft 120, as well as the prosthetic heart valve 114 in the collapsed state.

The delivery system 100 is operable to deliver or implant the prosthetic heart valve 114 as described in further detail below. FIGS. 1A and 1B illustrate the system 100 loaded with the prosthetic heart valve 114 prior to deployment. In particular, the prosthetic heart valve 114 is connected to the carrier shaft 120, for example via the coupling device 117, and is radially constrained within the sheath 104. The delivery system 100 is configured to be operable to transition from a loaded state in which the sheath 104 encompasses the prosthetic heart valve 114 to a deployed state in which the sheath 104 is withdrawn from the prosthetic heart valve 114 to permit the prosthetic heart valve 114 to self-expand to a natural arrangement and release from the delivery system 100, as described in further detail below.

The loaded delivery system 100 is advanced toward the implantation target site, for example in a retrograde manner through a cut-down to the femoral artery and into the patient's descending aorta. The delivery system 100 is then advanced, under fluoroscopic guidance, over the aortic arch, through the ascending aorta, and midway across the defective aortic valve (for aortic replacement). After positioning of the delivery system 100, the sheath 104 is partially retracted relative to the prosthetic heart valve 114 as shown in FIG. 1C. For example, the handle device 108 provided with the sheath assembly 106 is retracted toward the handle device 112 of the shaft assembly 110. As shown, a distal region 130 of the prosthetic heart valve 114 is thus exteriorly exposed relative to the sheath 104, and begins to self-expand and self-deploy. However, the self-expansion of the distal region 130 of the prosthetic heart valve 114 is controllably restrained in one embodiment by coupling structure 126 and tether 122. The prosthetic heart valve 114 is allowed to gradually self-expand by rotating coupling structure 126 in a first direction (e.g., in a clockwise direction) via the handle device 112. As the coupling structure 126 is rotated in the first direction, the end portion of the tether 122 attached to the coupling structure 126 moves in the proximal direction, which loosens the loop portion of the tether 122 attached to the distal end of the valve 114, and allows the distal end of the valve 114 to self-expand.

This proximal retraction of the sheath 104 and controlled expansion of the prosthetic heart valve 114 continues, with a continually increasing length of the prosthetic heart valve 114 being exposed and thus partially deployed, until the prosthetic heart valve 114 is fully deployed at the native heart valve. In one embodiment, continued rotation of the coupling structure 126 in the first direction causes the tether 122 to eventually slide off the proximal end of the coupling structure and thereby be released from the coupling structure 126. In this embodiment, the tether 122 remains attached to the prosthetic heart valve 114. In another embodiment, the tether 122 is configured to remain attached to the coupling structure 126 and is configured to be released from the prosthetic heart valve 114.

Prior to full deployment, the position of the prosthetic heart valve 114 relative to the implant site may also be evaluated when it is in a partially deployed state, such as that shown in FIG. 1C. In the event the clinician believes, based upon the above evaluation, that the prosthetic heart valve 114 should be repositioned relative to the implant site, the prosthetic heart valve 114 is first contracted or "resheathed".

The resheathing process according to one embodiment involves rotating coupling structure 126 in a second direction (e.g., in a counterclockwise direction) opposite the first direction via the handle device 112. As the coupling structure 126 is rotated in the second direction, the end portion of the tether 122 attached to the coupling structure 126 is pulled and moves in the distal direction, which reduces the size of the loop portion of the tether 122 attached to the distal end of the valve 114, and contracts the distal end of the valve 114. The sheath 104 is then advanced distally relative to the shaft assembly 110, and thus relative to the prosthetic heart valve 114. Distal movement of the sheath 104 continues until the prosthetic heart valve 114 is fully resheathed within the sheath 104. Once the prosthetic heart valve 114 is resheathed or recaptured, the system 100 can be repositioned relative to the implantation site, and the process repeated until the clinician is comfortable with the achieved positioning. Alternatively, the resheathed prosthetic heart valve 114 can be removed from the patient.

The delivery system 100 is useful with a variety of different configurations of a stented prosthetic heart valve. In general terms, the prosthetic heart valve 114 includes a stent frame maintaining a valve structure (tissue or synthetic), with the stent frame having a normal, expanded state and collapsible to a collapsed state for loading within the system 100. The stent frame can be constructed to self-deploy or self-expand when released from the delivery system 100, or a separate expansion member can be provided (e.g., an expansion balloon). For example, the prosthetic heart valve 114 can be a prosthetic sold under the trade name CoreValve® available from Medtronic CoreValve, LLC. Other non-limiting examples of transcatheter heart valve prostheses useful with the system 100 are described in U.S. Publication Nos. 2006/0265056; 2007/0239266; and 2007/0239269; the teachings of each of which are incorporated herein by reference.

Figure 2A:
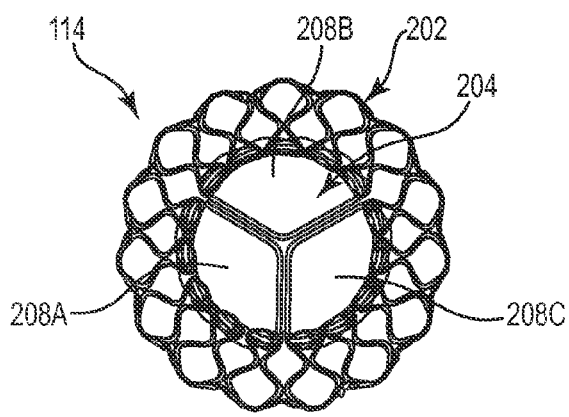
FIGS. 2A-2C are diagrams illustrating one embodiment of the prosthetic heart valve shown in FIGS. 1B and 1C.
Figure 2B:
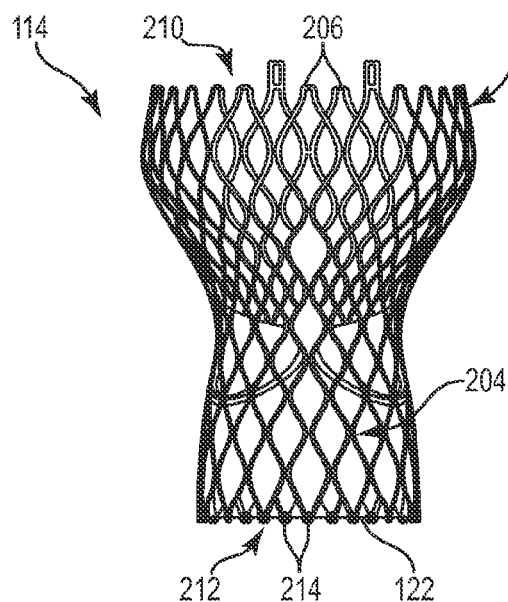
Figure 2C:
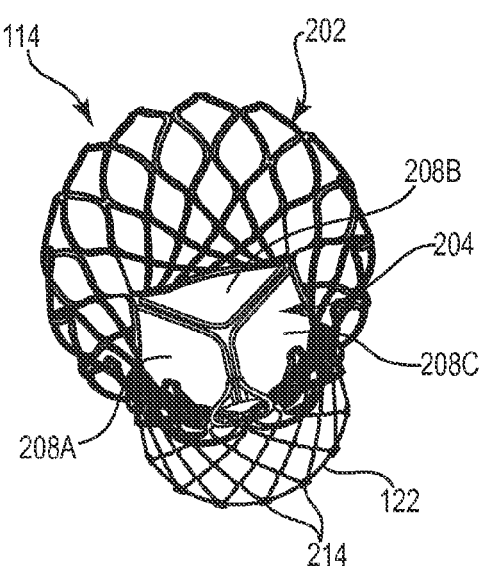

FIG. 2A is a diagram illustrating a top view of one embodiment of the prosthetic heart valve 114 shown in FIGS. 1B and 1C. FIG. 2B is a diagram illustrating a side view of the prosthetic heart valve 114 shown in FIG. 2A according to one embodiment. FIG. 2C is a diagram illustrating a perspective view of the prosthetic heart valve 114 shown in FIG. 2A according to one embodiment. Prosthetic heart valve 114 is compressible to a relatively small diameter for percutaneous delivery to the heart of a patient, and is then self-expandable via removal of external compressive forces. Prosthetic heart valve 114 according to one embodiment is self-expandable from a compressed arrangement to a natural arrangement As shown in FIGS. 2A-2C, prosthetic heart valve 114 includes a stent frame 202 and a valve structure 204. The stent frame 202 is a self-expanding support structure that includes a number of strut or wire portions 206 arranged relative to each other to provide a desired compressibility and strength to the prosthetic heart valve 114. Stent frame 202 can be made from a shape memory material, such as Nitinol. Valve structure 204 is mounted inside of the stent frame 202, and includes a plurality of leaflets 208A-208C (collectively referred to as leaflets 208). In the illustrated embodiment, valve structure 204 includes three leaflets 208. In other embodiments, valve structure 204 may include more or less than three leaflets 208. FIG. 2B also shows a proximal outflow end 210 and a distal inflow end 212 of prosthetic head valve 114. As shown in FIGS. 2B and 2C, the distal inflow end 212 of the prosthetic heart valve 114 includes a plurality of eyelets 214. Tether 122 is threaded through at least a subset of the eyelets 214 and forms a loop around the distal inflow end 212. As described above, the size of the loop is adjustable and is controlled by rotation of the coupling structure 126. In another embodiment, the distal end of the prosthetic heart valve 114 is an outflow end, and the tether 122 forms a loop around the distal outflow end.

FIG. 3 is a diagram illustrating a system 300 for delivering a transcatheter prosthetic heart valve 114 to an implantation site according to another embodiment. System 300 includes the same elements as system 100 (FIGS. 1A-1C), and additionally includes a second coupling structure 304 and a second sleeve 306, which are pad of the shaft assembly 110. The second sleeve 306 and the second coupling structure 304 are disposed at an intermediate portion of the shaft assembly 110. In the illustrated embodiment, the second coupling structure 304 is a coil spring. In one embodiment, the second sleeve 306 is a transparent tube. The proximal end of the prosthetic heart valve 114 is releasably coupled to the second coupling structure 304 via a second tether 302, such as a suture. In one embodiment, the tether 302 includes a first portion that forms a loop, which is attached to the proximal end of the prosthetic heart valve 114, and a second portion, which is attached to the second coupling structure 304. The second coupling structure 304 is configured to be rotated in a first direction (e.g., clockwise) to provide a controlled expansion of the proximal end of the prosthetic heart valve 114, and is configured to be rotated in a second direction (e.g., counterclockwise) to provide a controlled contraction of the proximal end of the prosthetic heart valve 114. In one embodiment, a clinician rotates the handle device 112 in a desired direction, which causes a corresponding rotation of the shaft assembly 110, including the second coupling structure 304.

In one embodiment, first coupling structure 126 or second coupling structure 304 may be coupled to a middle portion of the prosthetic heart valve 114 via a tether, and configured to be rotated in a first direction to provide a controlled expansion of the middle portion of the prosthetic heart valve 114, and configured to be rotated in a second direction to provide a controlled contraction of the middle portion of the prosthetic heart valve 114. In another embodiment, a third coupling structure is added to coupling structures 126 and 304, with the third coupling structure being coupled to a middle portion of the prosthetic heart valve 114 via a tether.

Figure 4:
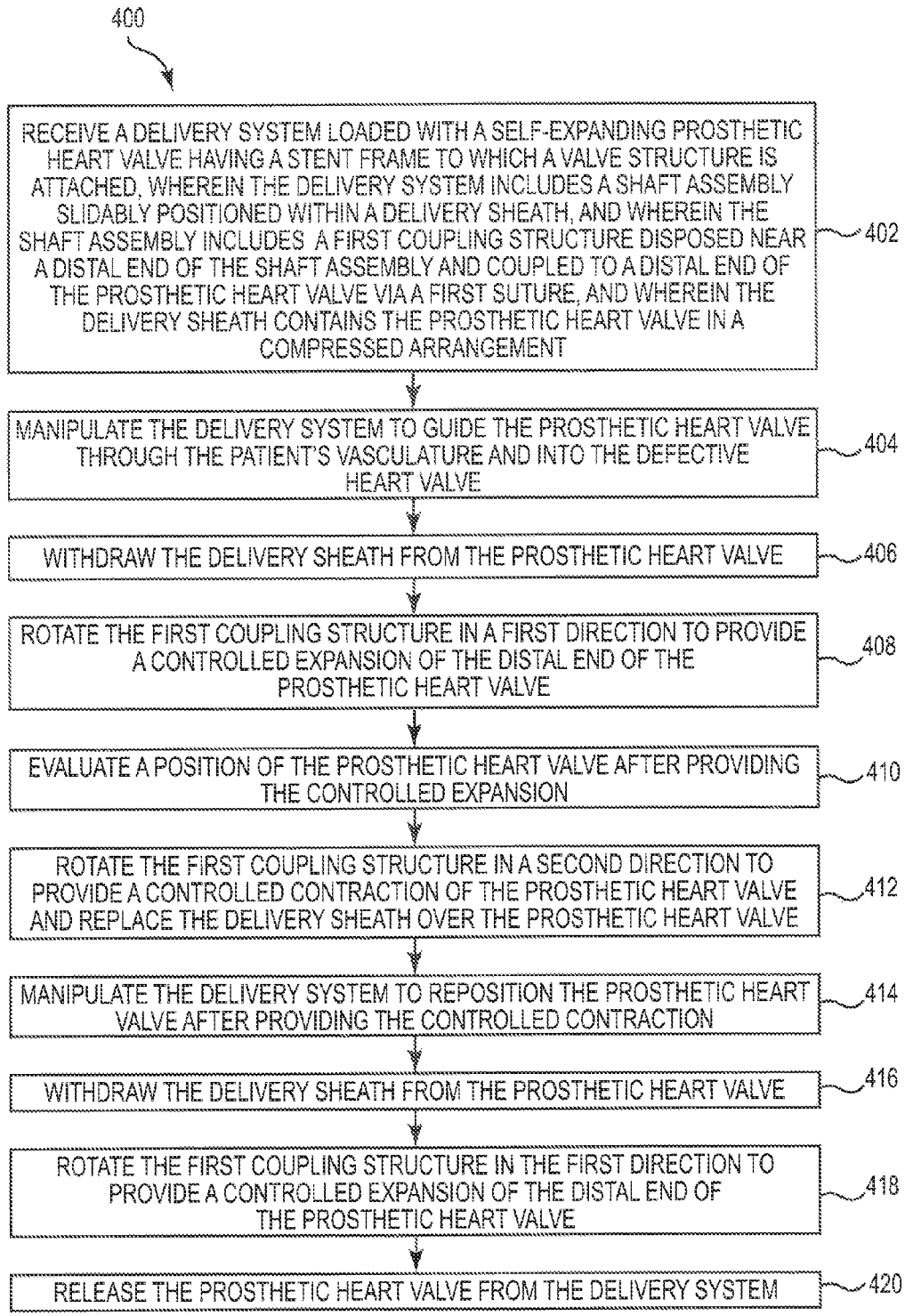
FIG. 4 is a flow diagram illustrating a method of performing a therapeutic procedure on a heart valve according to one embodiment.

FIG. 4 is a flow diagram illustrating a method 400 of performing therapeutic procedure on a defective heart valve of a patient according to one embodiment. In one embodiment, delivery system 100 (FIGS. 1A-1C) or delivery system 300 (FIG. 3) are configured to be used to perform method 400. At 402, a delivery system 100 loaded with a self-expanding prosthetic heart valve 114 having a stent frame 202 to which a valve structure 204 is attached is received, wherein the delivery system 100 includes a shaft assembly 110 slidably positioned within a delivery sheath 104, and wherein the shaft assembly 110 includes a first coupling structure 126 disposed near a distal end of the shaft assembly 110 and coupled to a distal end of the prosthetic heart valve 114 via a first tether 122, and wherein the delivery sheath 104 contains the prosthetic heart valve 114 in a compressed arrangement.

At 404 in method 400, the delivery system 100 is manipulated to guide the prosthetic heart valve 114 through the patient's vasculature and into the defective heart valve. At 406, the delivery sheath 104 is withdrawn from the prosthetic heart valve 114. At 408, the first coupling structure 126 is rotated in a first direction to provide a controlled expansion of the distal end of the prosthetic heart valve 114. At 410, a position of the prosthetic heart valve 114 is evaluated after providing the controlled expansion at 408. At 412, the first coupling structure 126 is rotated in a second direction to provide a controlled contraction of the prosthetic heart valve 114 and the delivery sheath 104 is replaced over the prosthetic heart valve 114. At 414, the delivery system 100 is manipulated to reposition the prosthetic heart valve 114 after providing the controlled contraction at 412. At 416, the delivery sheath 104 is again withdrawn from the prosthetic heart valve 114. At 418, the first coupling structure 126 is rotated in the first direction again to provide a controlled expansion of the distal end of the prosthetic heart valve 114. At 420, the prosthetic heart valve 114 is released from the delivery system 100.

In one embodiment of method 400, the shaft assembly 110 includes a second coupling structure 304 coupled to a proximal end of the prosthetic heart valve 114 via a second tether 302, and the method 400 further comprises rotating the second coupling structure 304 in the first direction to provide a controlled expansion of the proximal end of prosthetic heart valve 114.

Although the present disclosure has been described with reference to preferred embodiments, workers skilled in the art will recognize that changes can be made in form and detail without departing from the spirit and scope of the present disclosure.

What is claimed is:
1. A method of performing a therapeutic procedure on a defective heart valve of a patient, the method comprising:
receiving a delivery system loaded with a self-expanding prosthetic heart valve having a stent frame to which a valve structure is attached, the delivery system including a shaft assembly slidably positioned within a delivery sheath, the shaft assembly including a first coupling structure disposed near a distal end of the shaft assembly and coupled to a distal end of the prosthetic heart valve via a first tether, the delivery sheath containing the prosthetic heart valve in a compressed arrangement;
manipulating the delivery system to guide the prosthetic heart valve through the patient's vasculature and into the defective heart valve;
withdrawing the delivery sheath from the prosthetic heart valve to a partially retracted state in which an entirety of a distal region of the prosthetic heart valve is exposed and an entirety of a proximal region of the prosthetic heart valve is contained within the delivery sheath;

manipulating the first coupling structure in a first direction to provide a controlled expansion of the distal end of the prosthetic heart valve while in the partially retracted state; and releasing the prosthetic heart valve from the delivery system.

2. The method of claim 1, and further comprising:

evaluating a position of the prosthetic heart valve after providing the controlled expansion;

manipulating the first coupling structure in a second direction to provide a controlled contraction of the prosthetic heart valve; and manipulating the delivery system to reposition the prosthetic heart valve after providing the controlled contraction.

3. The method of claim 1, wherein the shaft assembly includes a second coupling structure coupled to a proximal end of the prosthetic heart valve via a second tether, and wherein the method further comprises:

manipulating the second coupling structure in a first direction to provide a controlled expansion of the proximal end of prosthetic heart valve.

4. The method of claim 3, wherein the step of manipulating the second coupling structure in a first direction to provide a controlled expansion of the proximal end of the prosthetic heart valve further comprises:

rotating the second coupling structure.

5. The method of claim 3, wherein the step of manipulating the second coupling structure in a first direction to provide a controlled expansion of the proximal end of the prosthetic heart valve comprises:

longitudinally translating the second coupling structure.

6. The method of claim 3, wherein the step of manipulating the second coupling structure in a first direction to provide a controlled expansion of the proximal end of the prosthetic heart valve comprises:

rotating and longitudinally translating the second coupling structure.

7. The method of claim 3, wherein the step of manipulating the second coupling structure to provide a controlled expansion of the proximal end of the prosthetic heart valve comprises:

manipulating the second coupling structure to control a size of a loop provided by the second tether around the proximal end of the prosthetic heart valve.

8. The method of claim 1, wherein the step of manipulating the first coupling structure in a first direction to provide a controlled expansion of the distal end of the prosthetic heart valve comprises:

rotating the first coupling structure.

9. The method of claim 1, wherein the step of manipulating the first coupling structure in a first direction to provide a controlled expansion of the distal end of the prosthetic heart valve comprises:

longitudinally translating the first coupling structure.

10. The method of claim 1, wherein the step of manipulating the first coupling structure in a first direction to provide a controlled expansion of the distal end of the prosthetic heart valve comprises:

rotating and longitudinally translating the first coupling structure.

11. The method of claim 1, wherein the step of manipulating the first coupling structure to provide a controlled expansion of the distal end of the prosthetic heart valve further comprises:

manipulating the first coupling structure to control a size of a loop provided by the first tether around the distal end of the prosthetic heart valve.

* * * * *